United States Patent [19]
Pachence et al.

[11] Patent Number: 6,080,194
[45] Date of Patent: Jun. 27, 2000

[54] MULTI-STAGE COLLAGEN-BASED TEMPLATE OR IMPLANT FOR USE IN THE REPAIR OF CARTILAGE LESIONS

[75] Inventors: James M. Pachence, Hopewell, N.J.; Sally Frenkel, Flushing; David Menche, New York, both of N.Y.

[73] Assignee: The Hospital for Joint Disease Orthopaedic Institute, New York, N.Y.

[21] Appl. No.: 08/385,290

[22] Filed: Feb. 10, 1995

[51] Int. Cl.[7] ...................................................... A61F 2/30
[52] U.S. Cl. ................................ 623/18; 623/11; 623/13; 606/151
[58] Field of Search ............................ 606/70, 151, 152; 623/11, 13, 18

[56] References Cited

U.S. PATENT DOCUMENTS

| | | | |
|---|---|---|---|
| 3,526,228 | 9/1970 | Lyng | 606/151 |
| 4,400,833 | 8/1983 | Kurland | 623/18 |
| 4,458,678 | 7/1984 | Yannas et al. . | |
| 4,505,266 | 3/1985 | Yannas et al. . | |
| 4,846,835 | 7/1989 | Grande . | |
| 5,306,311 | 4/1994 | Stone et al. . | |
| 5,380,328 | 1/1995 | Morgan | 606/70 |
| 5,480,436 | 1/1996 | Bakker et al. | 623/11 |

OTHER PUBLICATIONS

Ahmad, Frenkel, Casar, and Alexander; A mechanical testing technique for articular cartilage; a study of intrinsic repair, In: Advances in Bioengineering (Bidez, ed.) ASME, New York, pp. 245–251, 1991.

Amiel, Coutts, Harwood, Ishizue, and Kleiner: The Chondrogenesis of Rib Periochondrial Grafts for Repair of Full Thickenss Articular Cartilage Defects in a Rabbit Model, Connective Tissue Research 18:27–39 (1988).

Athanasiou, Schmitz, Schenck, Clem, Aufdermorte, Boyan: The Use of Biodegradable Implants for Repairing Large Articular Cartilage Defects in the Rabbit. Transactions of the 38th Annual Meeting of the ORS, p. 172, (1992).

Billings, von Schroeder, Mai, Aratow, Amiel, Woo, and Coutts; Cartilage resurfacing of the rabbit knee. Acta Orthop. Scand. 61(3); 201–206 (1990).

Convery, Akeson, Keown; The Repair of Large Osteochondral Defects, Clinical Orthopedics and Related Research 82:253–262 (1972).

Dahlberg and Kreicbergs; Demineralized Allogeneic Bone Matrix for Cartilage Repair, J. Orthop., Research 9:11–19 (1991).

Grande, Pitman, Peterson, Menche and Klein: The repair of experimentally produced defects in rabbit articular cartilage by autologous chondrocyte transplantation. Journal of Orthopedic Research 7:208–218 (1989).

Homminga, Bulstra, Bouwmeester and Van Der Linden; Perichondral Grafting for Cartilage Lesions of the Knee. The Journal of Bone and Joint Surgery 72:1003–1007 (1990).

Kimura, Yasui, Ohsawa and Ono; Chondrocytes Embedded in Collagen Gels Maintain Cartilage Phenotype During Long–Term Cultures. Clinical Orthopaedics 186:231–239 (1984).

(List continued on next page.)

*Primary Examiner*—Paul B. Prebilic
*Attorney, Agent, or Firm*—Caesar, Rivise, Bernstein, Cohen & Pokotilow, Ltd.

[57] ABSTRACT

The invention is a template to aid in the regeneration of articular cartilage. The template is formed by combining a porous collagen sponge ("collagen matrix") with a dense collagen membrane. The dense collagen membrane is placed on the surface of the cartilage defect to prevent cell migration from the subchondral plate and vasculature. The collagen membrane will allow movement and exchange of fluids, nutrients, cytokines and other factors necessary for cartilage regeneration. The collagen matrix has been developed to allow attachment and growth of cells, specifically chondrocytes which are normally found in articular cartilage. The collagen matrix can be combined with chondrocytes in vitro, and therefore serve to transport cultured cells to the defect site and to retain the cells in position following implantation. Procedures are described to effectively use the two-staged template, and to fix the template to the repair site.

16 Claims, 4 Drawing Sheets

OTHER PUBLICATIONS

Moran, Kim, Slater; Biological Resurfacing of Full–Thickenss Defects in Patellar Articular Cartilage of the Rabbit. Journal of Bone and Joint Surgery 74:659–667 (1992).

Nixon, Sams, Minor; Long–term Survival and Neocartilage Maturation Following Extensive Articular Resurfacing With Chondrocyte Laden Collagen Scaffolds, Transactions of the 40th Annual Meeting of the ORS, 1994.

Nixon, Sams, Lust, Grande and Mohammed; Temporal Matrix Synthesis and Histological Features of a Chondrocyte–Laden Porous Collagen Cartilage Analogue, American Journal of Veterinary Research 54:349–356 (1993).

Nixon, Lust and Vernier–Singer; Isolation, Propagation, and Cryopreservation of Equine Articular Chondrocytes. American Journal of Veterinary Research 53:2364–2370 (1992).

von Schroder, Kwan, Amiel and Coutts: The Use of Polylactic Acid Matrix and Periosteal Grafts for the Reconstruction of Rabbit Knee Articular Defects. Journal of Biomedical Materials Research 25:329–339 (1991).

Vachon, McIlwraith, Powers, McFadden and D.Amiel: Morphologic and Biochemical Study of Sternal Cartilage Autografts for Resurfacing Induced Osteochondral Defects in Horses. American Journal of Veterinary Research 53:1039–1047 (1992).

Weadock, Olson, and Silver: Evaluation of Collagen Crosslinking Techniques. Biomat, Med. Dev., Art, Org., 11(4), 293–318 (1983–84).

Homminga, Bulstra, Kuijer and Anton J. van der Linden: Repair of sheep articular cartilage defects with a rabbit costal perichondrial graft. Department of Orthopedics, University Hospital Masstricht, The Netherlands.

Robinson: Histologic Study of Articular Cartilage Repair in the Marmoset Condyle. J. Oral Maxillofac Surg. 51:1088–1094, 1993.

Grande, Singh and Pugh. Healing of Experimentally Produced Lesions in Articular Cartilage Following Chondrocyte Transplantation. The Anatomical Record 218:142–148 (1987).

FIG.2

MULTI-STAGE COLLAGEN-BASED TEMPLATE OR IMPLANT FOR USE IN THE REPAIR OF CARTILAGE LESIONS

FIELD OF THE INVENTION

This invention is within the technical fields of surgery, medicine, tissue engineering, biology, biomaterials, polymers, and biochemistry. It is both a product and a method of use for the repair of cartilage lesions, with and without the use of chondrocytes cultured in vivo.

BACKGROUND OF THE INVENTION

It has been well documented that injured articular cartilage has only a limited ability for self-repair. As articular cartilage is relatively avascular and aneural, loss of the surface tissue will result in a permanently scarred site. Lesions which fracture the subchondral bone which has a greater vascular supply will undergo an inflammation/repair response, with the damaged site filling with fibrocartilage tissue (Convery, et al. 1972). In either case, function is impaired and chronic pain is the usual prognosis as the biochemical and biomechanical characteristics of the cartilage have been altered. Current treatment protocols call for surgical intervention (such as abrasion arthroplasty, excision and drilling, articular cartilage debridement, and arthroscopic shaving) and will most often lead again to inadequate repair. Long-term morbidity such as degeneration to arthritic conditions will often result in patients with chronic cartilage problems.

Nevertheless, articular cartilage theoretically does have some intrinsic ability to heal after injury. For example, chondrocytes are capable of replication when isolated enzymatically from the cartilage matrix (Grande, et al., 1989). It has been suggested that cartilage repair can be initiated by either replication of chondrocytes in the regions adjacent to the defect, or by metaplasia of chondrocytes from other connective tissue stem cells within the joint capsule, such as from the synovium and subchondral bone (Sokoloff, 1978). Given this possibility, investigations of autograft or allograft tissue and tissue analogues to heal cartilage lesions has progressed.

Techniques were developed to utilize autologous tissue, such as transplantation of: 1) osteochondral graft (DePalma, et al., 1963); 2) chondrocytes (Grande, et al., 1989); 3) periosteum (Homminga, et al., 1990); and 4) demineralized bone (Dahlberg and Kreicbergs, 1991). These techniques have been used to transplant whole or partial joints, with mixed results. For example, a number of investigators attempted to heal cartilage defects using chondrocytes isolated from epiphyseal plates, as well as articular cells, with the hypothesis that these cells would have a greater chance of success due to their heightened metabolism (Itay, et al., 1987). Clinical studies using cultured cells reported excellent results, showing a significant decrease in pain and restoration of normal function after two to four years post-op (Iloika, et al., 1990; Ilomminga, et al., 1990).

Other investigations have used a combination of materials and autologous tissue to effectively repair cartilage defects, such as: 1) demineralized bone with perichondrium (Billings, et al., 1990); 2) polylactic acid matrices and periosteal grafts (von Schroeder, et al., 1991); and 3) bioresorbable meshes and chondrocytes (Freed, et al., 1993). Although these approaches gave repair tissue that more closely resembled normal cartilage than either the unfilled sites, or the sites filled with materials alone, it was evident that there was again a substantial amount of fibrocartilage formation.

In U.S. Pat. Nos. 4,505,266 and 4,458,678, Yannas et al. states in column 11 that various "types of fibrous lattices may be suitable for use as temporary prosthetic devices within most regions of the body, including skin, blood vessels, bones, connective tissue, contractile tissue and organs. Such lattices provide a structural system in which virtually any type of cell may grow, migrate and proliferate. They can be surgically emplaced within virtually any region of the body, and if properly seeded with the appropriate type(s) of cells, may allow for the regeneration of new tissue. For example, if a patient suffers damage to or disease of an organ, a portion of the organ may need to be removed. A fibrous lattice may be emplaced in the location created by removal of part of the organ. If a sufficient number of healthy cells from another part of that organ, or from a compatible donor, is seeded into the lattice by the methods of this invention, it may be possible to greatly promote the recovery and regeneration of the organ."

U.S. Pat. No. 4,846,835 discloses that chondrocytes that are grown in a three-dimensional collagen matrix can enhance the healing of articular cartilage lesions that do not fracture the subchondral plate.

In experiments in rabbits that followed the teachings of Yannas and Grande, cultured chondrocytes were seeded into a three-dimensional collagen matrix and the seeded matrix was implanted into a surgically-created articular cartilage lesion. Surprisingly, in view of those teachings, it was found that in addition to the presence of the desired hyaline-like cartilage, a substantial amount of undesirable fibro-cartilage was formed, apparently by fibroblasts that migrated into the matrix from the subchondral plate. Thus, these experiments indicate that neither Yannas nor Grande teach a method of forming a high quality hyaline-like cartilage suitable for repair of defects in articular cartilage because they do not provide a means to select against undesirable types of cells that can infiltrate the matrix from surrounding tissue. In the present invention, we have discovered a novel way to direct the growth of the desired hyaline-like cartilage, thus avoiding the difficulties of the prior art.

OBJECTS OF THE INVENTION

Accordingly, it is a general object of this invention to provide a multi-staged collagen implant to repair cartilage lesions which overcomes the disadvantages of the prior art.

It is a further object of this invention to provide a multi-staged collagen implant to repair cartilage lesions which is effective and safe.

It is another object of this invention to provide a multi-staged collagen implant to repair cartilage lesions which is resorbable.

SUMMARY OF THE INVENTION

Defects in articular cartilage can be healed by utilizing a regeneration template formed by combining a porous collagen sponge ("collagen matrix") with a dense collagen membrane. The dense collagen membrane is made with a pore size of less than 1 um (micrometer), and is cross-linked with a non-cytotoxic agent to increase strength and lengthen resorption time. Because of this dense collagen membrane, the invention can be used in full-thickness defects, including those which traverse the subchondral plate. The dense collagen membrane is placed on the surface of the cartilage defect to prevent cell migration from the subchondral plate and vasculature. The collagen membrane will allow movement and exchange of fluids, nutrients, cytokines and other factors necessary for cartilage regeneration. The collagen matrix is placed on top of the dense collagen membrane. The collagen matrix has a pore size of between 50–200 micrometers and allows the attachment of cells, specifically, chondrocytes.

DESCRIPTION OF THE DRAWINGS

Other objects and many attendant features of this invention will become readily appreciated as the same becomes better understood by reference to the following detailed description when considered in connection with the accompanying drawings wherein:

FIG. 1 shows the anatomy of normal cartilage and a defect or wound site 4 in which the following reference characters appear:

1 representing the articular surface, 2 hyaline cartilage 3 cancellous bone and marrow, 4 defect, 5 extracellular matrix, 6 chondrocytes, 7 tidemark, 8 calcified cartilage and 9 the subchondral plate.

DESCRIPTION OF THE PREFERRED EMBODIMENTS

Defects in articular cartilage can be healed by utilizing a template 12 formed by combining a porous collagen sponge ("collagen matrix") 13 with a dense collagen membrane 14.

The dense collagen membrane 14 is made with a pore size of less than one micrometer and is cross-linked with a non-cytotoxic agent to increase strength and lengthen resorption time. Because of this dense collagen membrane 14, the template 12 can be used in full-thickness defects 4, including those which traverse the subchondral plate 9. The dense collagen membrane 14 is placed on the surface of the cartilage defect 4 to prevent cell migration from the subchondral plate 9 and vasculature. The collagen membrane 14 will allow movement and exchange of fluids, nutrients, cytokines and other factors necessary for cartilage regeneration.

A collagen template 12 has been developed to allow attachment and growth of cells, particularly chondrocytes 6. In vitro studies have been used to determine the optimal pore size of the porous collagen matrix 13 component of the template 12. The collagen matrix 13 can be used to immobilize chondrocytes 6 in vitro and support subsequent cell growth. The cell number can then be expanded in vitro, and the collagen matrix 13 can be used transport the cells to the repair site 4 and to retain the cells in position following implantation.

The collagen matrix component 13 of the template 12 has been developed to allow attachment and growth of cells, particularly chondrocytes 6. In vitro studies have been used to determine the optimal pore size of the porous collagen matrix component 13 of the template 12. The collagen matrix 13 can be used to immobilize chondrocytes 6 in vitro and support subsequent cell growth. The cell number can then be expanded in vitro, and the collagen matrix can be used to transport the cells to the repair site and retain the cells in position following implantation.

Previous studies have shown that the collagen matrix 13 pore size can be controlled by varying the dispersion pH, collagen concentration and the lyophilization cycle (freezing time, temperature range, and cycle time (Dillion et al. 1986)). See also U.S. Pat. No. 4,522,753. The collagen matrices have also been characterized according to their permeability to globular macromolecules. For example, it was found that a pore structure of approximately 15 micrometers would exclude molecules greater than $10^6$ daltons; a dense collagen membrane had a molecular weight exclusion of $7 \times 10^4$ daltons (Li, 1987). Chondrocytes were grown on type I collagen matrices of varied pore structure in order to determine the effect of the average matrix pore size on cellular growth rate. It was found that the pore structure did not affect the rate of cell growth after 12 days. However, chondrocyte infiltration was greater for average pore sizes greater than 100 micrometers. A parallel study using fibroblasts showed similar cell growth results. It is important to note that the growth rate of fibroblasts on the dense collagen membrane was approximately the same as a porous matrix, but that migration of cells through the membrane was excluded (Pachence et al., 1991).

The dense collagen membrane 14 can be attached to the collagen matrix 13 prior to cell culture or prior to implantation, using: 1) bioresorbable sutures; or 2) a fusing technique, requiring that the dense collagen membrane 14 be incorporated into the collagen matrix 13 during formation.

It has been shown through a series of in vivo studies that the template 12 with and without the addition of chondrocytes 6 promotes the healing of surgically induced full thickness defects in a rabbit model of cartilage damage. The chondrocyte-seeded templates have been proven, through the use of histologic, biochemical, and mechanical analyses of retrieved implant-tissue sites, to result in repair tissue which appears to be hyaline cartilage.

Figure 1:
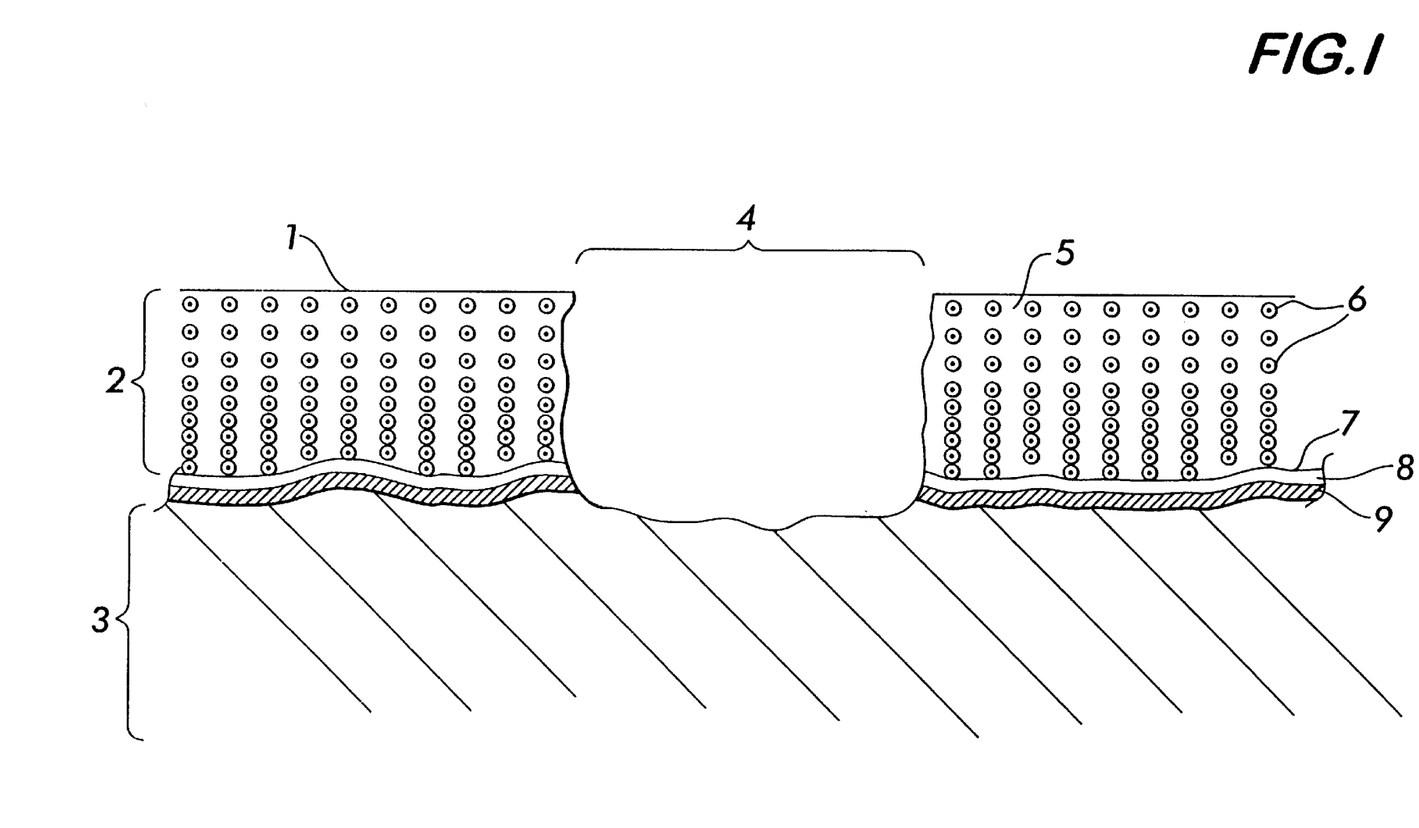
Figure 2:
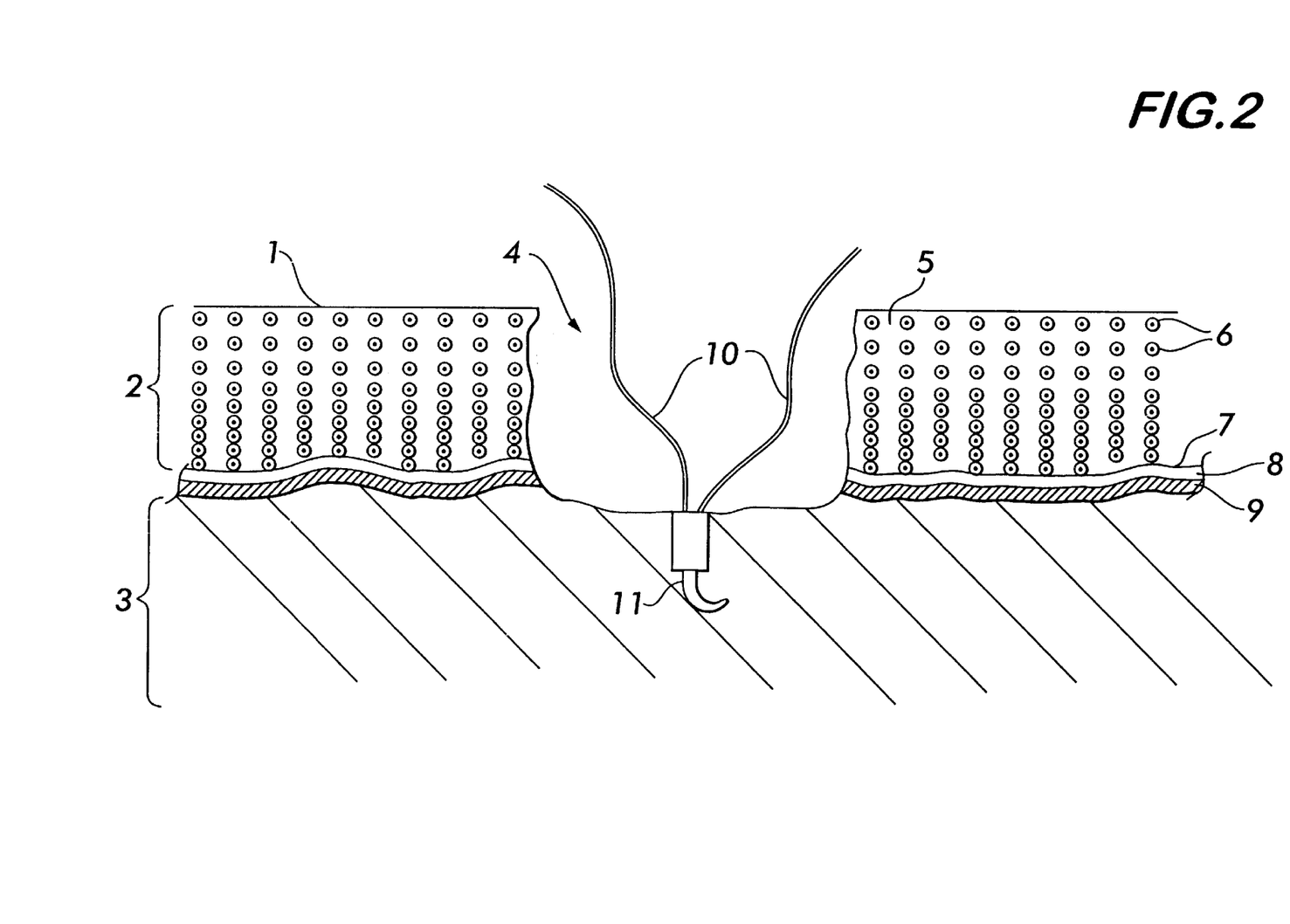
FIG. 2 shows an anchor 11 with attached suture lines 10 embedded into the bone 3 at the defect site 4.
Figure 3:
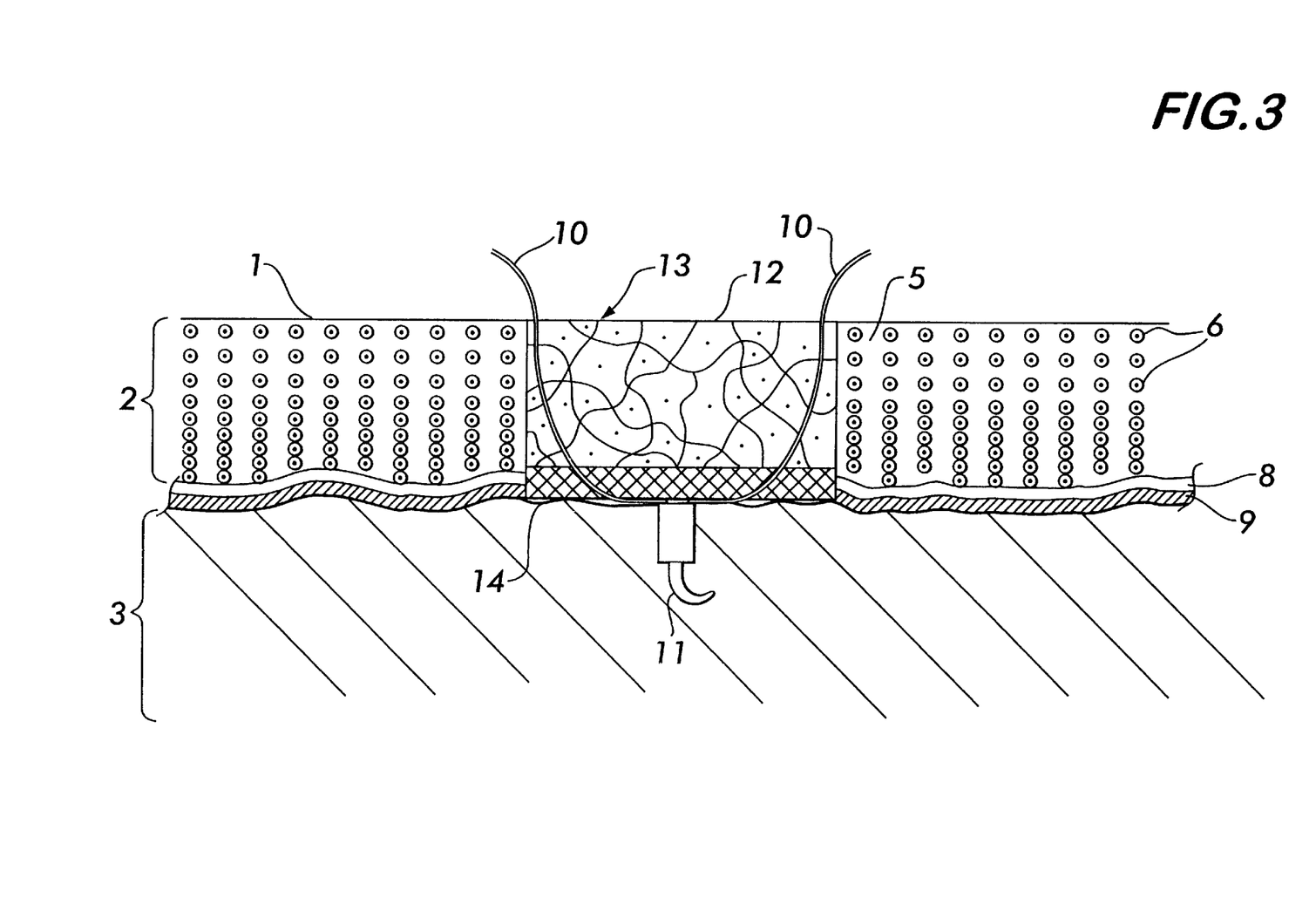
FIG. 3 shows the positioning of the collagen template 12 with the porous collagen matrix 13 and the dense collagen membrane 14 in threading the anchored sutures 10 through the template 12.

As shown in FIGS. 1–3, the orientation of the template 12 in the cartilage defect 4 is fundamental to achieve a successful result. The dense layer 14 is placed "downward" into the defect 4, contacting bone 3, and the porous layer 13 lies in the plane of the natural cartilage. The dense layer 14 has been shown experimentally to inhibit the formation of fibrocartilage. The thicknesses of the components of the template 12 can vary depending upon the circumstances of use. For example, the thickness of the dense collagen membrane may be in the range of 50 to 200 micrometers or more and the thickness of the porous collagen matrix may be in the range of 0.5 to 8 millimeters or more.

Figure 4:
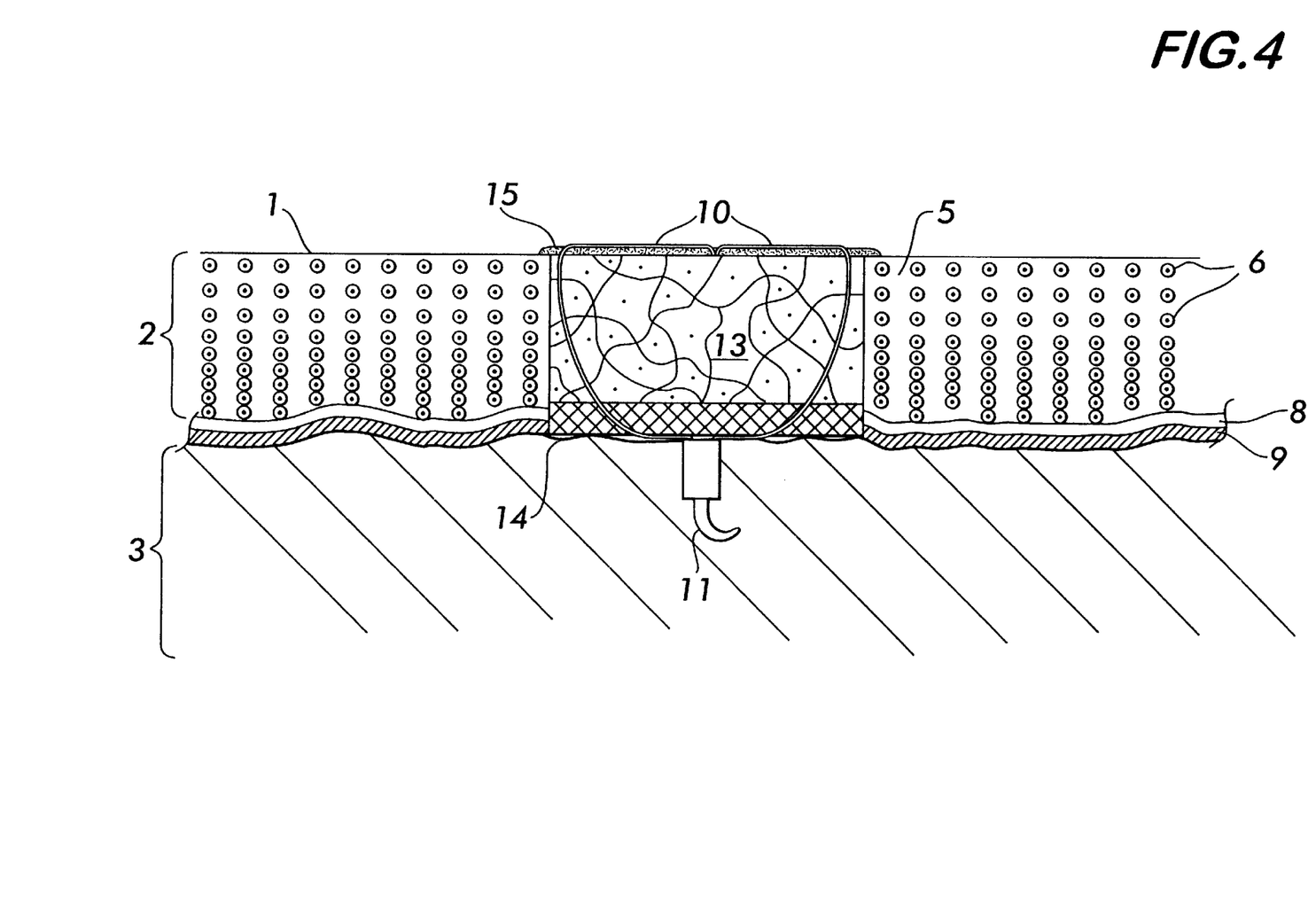
FIG. 4 shows the positioning of a top protective layer 15 in securing this layer 15 and template 12 with anchoring sutures 10.

Methods of surgical fixation for a cartilage repair material 12 are important, as movement of the joint can dislodge the implant prior to healing. For the present invention, an attachment method is used to hold the collagen matrix 13 and dense collagen membrane 14 into place. The method consists of anchoring sutures 10 through the subchondral plate 9 into bony tissue 3, with at least two lines 10 emerging from the surface. The anchored suture lines 10 are then pulled through the collagen implant 12 at its four quadrants, and is thus used to secure the cartilage repair material 12 into the wound site 4. In some instances, as shown in FIG. 4, a piece of autologous periosteum 15 is placed over the top of the collagen matrix 13, and is also secured by the anchored suture lines 10.

EXAMPLE 1

Preparation and Characteristics of the Porous Matrix

A collagen matrix is formed, using standard methods as described in U.S. Pat. No. 5,206,028, the entire disclosure of which is incorporated by reference herein. The matrix has an average pore structure of between 50 to 200 micrometers, preferably 150 micrometers. Type I collagen is dispersed in a 0.5% lactic acid solution, with a final collagen concentration of 0.7% by weight. The collagen dispersion is forced through a 100 mesh size stainless steel filter, then poured onto stainless steel trays to a thickness of about 4 mm. The dispersion is frozen for two hours at −35° C. before a vacuum is applied. The frozen dispersion is then lyophilized under a 100 micron vacuum for 48 hours, with the temperature increasing to 20° C. The shelf temperature is subsequently raised to 25° C. for an additional 24 hours to complete the cycle. The collagen matrix is cross-linked using a non-cytotoxic agent, or physical method previously described (Weadock, et al, 1983). For example, the collagen matrix can be subjected to a vaporized formaldehyde (5% solution). Cross-linking by this method allows the implant to stay intact for four to eight weeks.

EXAMPLE 2
Preparation and Characteristics of the Dense Collagen Membrane

A dense collagen membrane is prepared according to the procedure presented in U.S. Pat. No. 5,206,028, the entire disclosure of which is incorporated by reference herein. A porous matrix, having a thickness of 4 mm to 10 mm, is hydrated using a humidity controlled chamber, relative humidity of 80% at 25° for 60 minutes. The moist collagen material is compressed between two Teflon sheets to a thickness of less than 0.2 mm. The compressed material is then cross-linked in a solution of 0.5% formaldehyde, 1% sodium bicarbonate at pH 8 to 60 minutes. The cross-linked membrane is then raised thoroughly with water, then freeze dried overnight under similar conditions as in Example 1, except that the time for freeze drying is about 48 hours. The dense collagen membrane has an inner construction of densely packed fibers that are intertwined in a mufti-layer structure. The collagen membrane allows diffusion of molecules of at least $10^5$ MW, but will not allow penetration by fibroblasts.

EXAMPLE 3
Utilization of Non-cell Seeded Matrix in Cartilage Defects

1. Prepare a surgically defined site, slightly smaller than the size of the matrix implant. The depth should be approximately the same size of the collagen matrix/cell composite. The surgically prepared site should go through the subchondral plate (i.e., a bleeding bed).
2. Set an anchor, with two attached resorbable suture lines, into the center of the surgically prepared site (FIG. 2). There will be four lines available, one in each quadrant.
3. Attach a dense collagen membrane (pore structure less than one micrometer) onto the collagen matrix, using resorbable sutures such as Vicryl 7-0 (FIG. 3).
4. Place the template with the dense collagen membrane on the bottom of the surgically prepared site, securing it in place with the suture lines by threading the suture lines through the template.
5. Place a protecting piece of tibial periosteum over the matrix. The periosteum must be oriented over the implant as follows. The cambium layer is oriented facing the implant (downward into the defect), and the fibrous layer faces the articular surface (upward into the joint space). Pull the suture line through the periosteum, tie the sutures over top of the protecting sheet (FIG. 4).

EXAMPLE 4
Utilization of Cell-Seeded Matrix in Cartilage Defects

1. Obtain autologous sample of tissue containing cartilage or progenitor cells.
2. Remove extracellular matrix from the tissue sample, then isolate cells using standard methods.
3. Expand cells in culture.
4. The dense collagen membrane is attached to the collagen matrix with bioresorbable sutures, such as Vicryl 7-0.
5. Add cells to the pore-defined collagen matrix, so that cells penetrate through the matrix. This can be done by laying the cell suspension over the matrix, then carefully applying a vacuum under the matrix.
6. Culture the collagen template/cell composite for one week or more.
7. Prepare a surgically defined site, slightly smaller than the size of the implant. The depth should be approximately the same size of the collagen template/cell composite. The surgically prepared site should go through the subchondral plate (i.e., a bleeding bed).
8. Set an anchor, with two attached resorbable suture lines, into the center of the surgically prepared site (FIG. 2). There will be four lines available, one in each quadrant.
9. Place the collagen template/cell composite onto the bottom of the surgically prepared site, with the dense collagen membrane component in contact with the bottom, and thread the membrane with the suture lines (FIG. 3).
10. Place a protecting sheet of either clear collagen, or a piece of tibial periosteum over the matrix component of the template. The clear collagen piece is an air dried film with a thickness of 50–200 micrometers, the film being made by drying a one percent collagen dispersion in a non-stick tray. If periosteum is used, it is oriented over the implant as follows: the cambium layer is oriented facing the implant (downward into the defect), and the fibrous layer faces the articular surface (upward into the joint space). Pull the suture line through the matrix and the collagen sheet or periosteum, tie the sutures over top of the protecting sheet (FIG. 4).

Without further elaboration the foregoing will so fully illustrate our invention that others may, by applying current or future knowledge, adapt the same for use under various conditions of service.

The following publications involve some of the experiments used in testing portions of the invention, without disclosing the multi-stage device.

Grande, Vachon; Repair of induced osteochondral defects with a composite chondro-cyte/collagen allograft in dogs. Transactions of the Combined Meeting of the Orthopaedic Research Societies of USA, JAPAN, and CANADA, Oct. 21–23, 1991, Banff, Alberta.

Pachence, Frenkel, Lin: Development of a tissue analog for cartilage repair. In: Tissue Inducing Biomaterials (Cima, Ron, eds.) Materials Research Society Press, Pittsburgh, 1991.

Ahmad, Frenkel, Casar, and Alexander; A mechanical testing technique for articular cartilage; a study of intrinsic repair, In: Advances in Bioengineering (Bidez, ed.) ASME, New York, pp 245–251, 1991.

Frenkel, Pachence, Alexander; Optimization of a cell-seeded collagen implant for cartilage repair. Transactions of the Orthopaedic Research Society 18:730, 1993.

Toolan, Frenkel, Pachence, Yalowitz, Ahmad, Casar; In vitro characterization of a collagen chondrocyte composite matrix for cartilage repair, Transactions of the Society for Biomaterials 17:313, 1994.

Toolan, Frenkel, Pachence, Yalowitz and Alexander: An analysis of a chondrocyte-collagen implant for cartilage repair. Journal of Bone and Joint Surgery, abstract in press.

Frenkel, Pachence, Toolan, Menche, Pitman, Crawford, Steger; Evaluation of a novel two-layered collagen implant for articular cartilage repair in a rabbit model. Journal of Bone and Joint Surgery, abstract in press (to be presented at the Annual Meeting of the Orthopaedic Research Society, Orlando, 1995).

Other referenced articles:

Amiel, Coutts, Harwood, Ishizue, and Weiner: The Chondrogenesis of Rib Periochondrial Grafts for Repair of Full Thickenss Articular Cartilage Defects in a Rabbit Model, Connective Tissue Research 18:27–39 (1988).

Athanasiou, Schmitz, Schenck, Clem, Aufdermorte, Boyan: The Use of Biodegradable Implants for Repairing Large Articular Cartilage Defects in the Rabbit. Transactions of the 38th Annual Meeting of the ORS, p. 172, (1992).

Bentley, Smith and Mukerjhee, Isolated Epiphyseal Chondrocyte Allografts into Joint Jurfaces; An Experimental Study in Rabbits. Ann. Rheum. Dis. 37;449–458 (1978).

Billings, von Schroeder, Mai, Aratow, Amiel, Woo, and Coutts; Cartilage resurfacing of the rabbit knee. Acta Orthop. Scand. 61(3); 201–206 (1990).

Convery, Akeson, Keown; The Repair of Large Osteochondral Defects, Clinical Orthopedics and Related Research 82:253–262 (1972).

Coutts, Yoshioka, Amiel, Hacker, Harwood, and Monosov; Cartilage repair using a porous polylactic acid matrix with allogeneic perichondrial cells. Transactions of the 40th Annual Meeting of the ORS, 1994.

Dahlberg and Kreicbergs; Demineralized Allogeneic Bone Matrix for Cartilage Repair, J. Orthop. Research 9:11–19 (1991).

DePalma, Tsa-Hos, and Maaler; Viability of Osteochondral Grafts as Determined by Uptake of $S^{35}$, J. Bone Joint Surg. 45A: 1565–1578 (1963).

Freed, Marquis, Nohria, Emmanual, Mikos and Langer; Neocartilage formaton in vitro and in vivo using cells cultured on synthetic biodegradable polymers. Journal of Biomedical Materials Research 27:11–23 (1993).

Grande, Pitman, Peterson, Menche and Klein: The repair of experimentally produced defects in rabbit articular cartilage by autologous chondrocyte transplantation. Journal of Orthopedic Research 7:208–218 (1989).

Hogervorst, Meijer and Klopper: The effect of a TCP-collagen implant on the healing of articular cartilage defects in the rabbit knee joint. Journal of Applied Biomaterials 3:251–258 (1992).

Hoikka, Jaroma and Ritsila, Reconstruction of the Patellar Articulation with Periosteal Grafts, Acta Orthop. Acad. 61:36–39 (1990).

Homminga, Bulstra, Bouwmeester and Van Der Linden; Perichondral Grafting for Cartilage Lesions of the Knee. The Journal of Bone and Joint Surgery 72:1003–1007 (1990).

Hunziker and Rosenberg; Induction of repair in partial thickness articular cartilage lesions by timed release of TGFb. Transactions of the 40th Annual Meeting of the ORS, 1994.

Itay, Abramovici and Nevo; Use of cultured embryonal chick epiphyseal chondrocytes as grafts for defects in chick articular cartilage. Clinical Orthopaedics and Related Research 220:294–303 (July 1987).

Kimura, Yasui, Ohsawa and Ono; Chondrocytes Embedded in Collagen Gels Maintain Cartilage Phenotype During Long-Term Cultures. Clinical Orthopaedics 186:231–239 (1984).

Messner: Hydroxylapatite supported dacron plugs for repair of isolated full-thickness defects of the rabbit femoral condyle. Transactions of the 40th Annual Meeting of the ORS, 1994.

Moran, Kim, Slater; Biological Resurfacing of Full-Thickenss Defects in Patellar Articular Cartilage of the Rabbit. Journal of Bone and Joint Surgery 74:659–667 (1992).

Nixon, Sams, Minor; Long-term Survival and Neocartilage Maturation Following Extensive Articular Resurfacing With Chondrocyte Laden Collagen Scaffolds, Transactions of the 40th Annual Meeting of the ORS, 1994.

Nixon, Sams, Lust, Grande and Mohammed; Temporal Matrix Synthesis and Histological Features of a Chondrocyte-Laden Porous Collagen Cartilage Analogue, American Journal of Veterinary Research 54:349–356 (1993).

Nixon, Lust and Vernier-Singer; Isolation, Propagation, and Cryopreservation of Equine Articular Chondrocytes. American Journal of Veterinary Research 53:2364–2370 (1992).

Rich, Johnson, Zhou and Grande: The use of periosteal cell/polymer tissue constructs for the repair of articular cartilage defects. Transactions of the 40th Annual Meeting of the OHS, 1994.

Robinson, Efrat, Mendes, Halperin, Nevo; Implants composed of carbon fiber mesh and bone-marrow-derived chondrocyte-enriched cultures for joint surface reconstruction. Bulletin of the Hospital for Joint Diseases 53(1)1–8 (Spring 1993).

von Schroder, Kwan, Amiel and Coutts: The Use of Polylactic Acid Matrix and Periosteal Grafts for the Reconstruction of Rabbit Knee Articular Defects. Journal of Biomedical Materials Research 25:329–339 (1991).

Sokoloff: In Vitro Culture of Skeletal Tissues, Chapt, 1, in *The Joints and Synovial Fluid (Vol. II)*, edited by L. Sokoloff (Academic Press, NY, 1978), pp. 1–27.

Vachon, McIlwraith, Powers, McFadden and D.Amiel: Morphologic and Biochemical Study of Sternal Cartilage Autografts for Resurfacing Induced Osteochondral Defects in Horses. American Journal of Veterinary Research 53:1039–1047 (1992).

Wakitani, Kimura, Hirooka, Ochi, Yoneda, Yasui, Owaki, Ono; Repair of rabbit articular surfaces with allograft chondrocytes embedded in collagen gel. British Journal of Bone and Joint Surgery 71-13;74-80 (1989).

Wakitani, Ono, Goldberg and Caplan; Repair of large cartilage defects in weight-bearing and partial weight-bearing articular surfaces with allograft articular chondrocytes embedded in collagen gels. Transactions of the 40th Annual Meeting of the ORS, 1994.

Weadock, Olson, Silver: Evaluation of Collagen Crosslinking Techniques, Biomat, Med.Dev.Art. Org. 11 :293–318 (1983).

RELATED REFERENCES

U.S. Pat. No. 4,458,678 Cell Seeding Procedures Involving Fibrous Lattices (Yannas and Burke)

U.S. Pat. No. 4,505,266 Cell Seeding Procedures Involving Fibrous Lattices (Yannas and Burke)

U.S. Pat. No. 4,846,835 Technique for healing lesions in cartilage (Grande)

U.S. Pat. No. 5,108,438 Prosthetic intervertebral disc acting as a regrowth scaffold (Stone)

U.S. Pat. No. 5,041,138 Formation of cartilage structures by attaching chondrocyte cells to biocompatible matrix in nutrient environment (Vacanti, et al.)

U.S. Pat. No. 5,053,050 Compositions for Repair of Cartilage and Bone (Itay)

U.S. Pat. No. 5,133,755 Method and Apparatus for Biodegradable Osteogenic Bone Graft Substitute Device (Brekke)

U.S. Pat. No. 5,206,023 Method and Compositions for the Treatment and Repair of Defects or Lesions in Cartilage (Hunziker)

U.S. Pat. No. 5,206,028 Dense Collagen Membrane Matrices for Medical Use (Shu-Tung Li)

U.S. Pat. No. 4,837,379 Tissue equivalent comprising fibrin containing hydrated collagen lattice contracted with e.g., fibroblasts, opt. in multilayer form, useful as organ or tissue replacements (Weinberg)

WO 8907425 Medical use of amniotic cells or tissue for tissue regeneration, implant treatment, production of useful substances, detoxification of body fluids and skin or scalp treatment (Butler, et al.)

EP 277678 Graft for reconstructive surgery comprises pref. biodegradable prods. organic polymer matrix with bimodal pore size distribution (Nijenhuis, et al.)

WO 8803785 Artificial matrix for controlled cell growth used for chimeric neomor-phogenesis of organs by controlled cellular implantation (Vacanti & Langer)

WO 8301384 Tissue generation at wounds by placing fibrous lattice in contact with wound and seeding lattice with cells (Yannas & Burke)

We claim:

1. A template for the repair of cartilage defects leading to the regeneration of hyaline-like cartilage, the template comprising:
   a) a first layer comprising a dense collagen membrane having a pore size of less than 1 micrometer which is cross-linked with a non-cytotoxic agent to increase strength and lengthen resorption time, to provide a barrier against movement of cells from the subchondral plate, the membrane being sufficiently permeable to allow the passage therethrough of fluids, nutrients, cytokines, and other endogenous factors necessary for healing; and
   b) a second layer secured to the first layer and comprising a porous collagen matrix having pore size of 50 to 200 micrometers, which permits the ingrowth of cells.

2. The template of claim 1 additionally comprising autologous periosteum placed on top of the collagen matrix and the matrix is initially devoid of cells.

3. The template of claim 1 additionally comprising a collagen film placed on top of the collagen matrix and the matrix is initially devoid of cells.

4. The template of claim 1 additionally comprising chondrocyte cells cultured ex vivo with the porous collagen matrix so that the chondrocytes permeate the collagen matrix.

5. The template of claim 4 additionally comprising a piece of autologous periosteum placed on top of the collagen matrix containing the chondrocyte cells.

6. The template of claim 4 additionally comprising a collagen film placed on top of the collagen matrix containing the chondrocyte cells.

7. The template of claim 1 wherein the dense collagen membrane is attached to the collagen matrix using a resorbable suture.

8. The template of claim 1 wherein the dense collagen membrane is incorporated into the collagen matrix during formation of the matrix.

9. The template of claim 1 wherein the dense collagen membrane has a thickness in the range of 50 to 200 micrometers.

10. The template of claim 1 wherein the porous collagen matrix has a thickness in the range of 0.5 to 8 millimeters.

11. A method of attaching the template of claim 1 into place in a wound site in a living being, the method comprising the steps of:
    a) securing anchoring sutures through a subchondral plate into bony tissue, with a plurality of suture lines emerging therefrom; and
    b) utilizing the anchored suture lines to secure the template to the wound site.

12. The method of claim 11 additionally comprising the step of selecting the plurality of suture lines to be two to four in number.

13. The method of claim 11 additionally comprising the steps of:
    a) selecting the template to additionally comprise autologous periosteum placed on top of the collagen matrix and the matrix is initially devoid of cells; and
    b) utilizing the method to attach the periosteum, collagen matrix and dense collagen membrane to the wound site.

14. The method of claim 11 additionally comprising the steps of:
    a) selecting the template to additionally comprise collagen film placed on top of the collagen matrix and the collagen matrix is initially devoid of cells;
    b) attaching the collagen film, collagen matrix and dense collagen membrane to the wound site by the method.

15. The method of claim 11 additionally comprising the steps of:
    a) selecting the template to comprise periosteum, collagen matrix with cells and dense collagen membrane; and
    b) the method is utilized to secure the material to the wound site.

16. The method of claim 11 additionally comprising the steps of:
    a) selecting the template to comprise collagen film, collagen matrix with cells and dense collagen membrane; and
    b) the method is utilized to secure the template to the wound site.

* * * * *